(12) United States Patent
Carelli et al.

(10) Patent No.: US 8,802,815 B2
(45) Date of Patent: Aug. 12, 2014

(54) PEPTIDES AND USES THEREOF TO MODULATE IGF-1 SYNTHESIS AND IGF-1 RECEPTOR EXPRESSION

(75) Inventors: Claude Carelli, Suresnes (FR); Zvi Laron, Ramat Efal (IL); Gila Maor, Kiriat-motzkin (IL)

(73) Assignee: Universite Pierre et Marie Curie (Paris 6), Paris (FR)

( * ) Notice: Subject to any disclaimer, the term of this patent is extended or adjusted under 35 U.S.C. 154(b) by 0 days.

(21) Appl. No.: 13/257,332

(22) PCT Filed: Mar. 18, 2010

(86) PCT No.: PCT/FR2010/050490
§ 371 (c)(1),
(2), (4) Date: Feb. 28, 2012

(87) PCT Pub. No.: WO2010/106294
PCT Pub. Date: Sep. 23, 2010

(65) Prior Publication Data
US 2012/0149640 A1    Jun. 14, 2012

(30) Foreign Application Priority Data
Mar. 19, 2009   (FR) ..................................... 09 51754

(51) Int. Cl.
*A61K 38/00* (2006.01)
*A61K 38/04* (2006.01)
*A61K 38/31* (2006.01)
*C07K 5/00* (2006.01)
*C07K 7/00* (2006.01)
*C07K 16/00* (2006.01)
*C07K 17/00* (2006.01)

(52) U.S. Cl.
USPC ............ 530/300; 530/311; 530/325; 530/326

(58) Field of Classification Search
None
See application file for complete search history.

(56) References Cited

PUBLICATIONS

Gallagher, 2010, Trends Endocrinology Metabolism, vol. 21, Issue 10, pp. 610-618.*
Kolchanov, 1988, Journal of Molecular Evolution, vol. 27, pp. 154-162.*
Pasquo, 2012, PLoS One, vol. 7, Issue 2, e32555.*
Grace, et al. "Novel sst2-selective somatostatin agonists. Three-dimensional consensus structure by NMR" *Journal of Medicinal Chentistiy*, vol. 49, No. 15 (2006) pp. 4487-4496.
Pandit, et al. "Self-assembly of the octapeptide lanreotide and lanreotide—based derivatives; the role of the aromatic residues" *Journal of Peptide Science*, vol. 14, No. 1 (2008) pp. 66-75.

* cited by examiner

*Primary Examiner* — Robert Landsman
(74) *Attorney, Agent, or Firm* — Cesari and McKenna, LLP

(57) ABSTRACT

The invention relates to peptides for modulate IGF-1 activity, a pharmaceutical composition comprising them as well as their applications as medicinal products and cell proliferation modulating agents in vitro.

10 Claims, 4 Drawing Sheets

Control     P70 $10^{-6}$ M     P70 $10^{-7}$ M

Control     P70 $10^{-6}$ M     P70 $10^{-7}$ M

US 8,802,815 B2

PEPTIDES AND USES THEREOF TO MODULATE IGF-1 SYNTHESIS AND IGF-1 RECEPTOR EXPRESSION

CROSS REFERENCE TO RELATED APPLICATIONS

This application claims the priority of international application no. PCT/FR2010/050490, filed on Mar. 18, 2010, which claims the priority of French application no. 0951754, filed on Mar. 19, 2009. The contents of both application are incorporated herein by reference.

The invention relates to peptides that are modulators of IGF-1.

TECHNICAL BACKGROUND

The cancerous process, which manifests in an uncontrolled cell proliferation, is often the reflect of growth factors and/or growth factors receptors overexpression in one and the same cell (Moyse et al. 1985, Cassoni et al. 2006, Hanahan et al. 2000).

Numerous factors, acting in network, are responsible for cell cycle progression and cell proliferation. In particular, a group of these factors, called "growth factors", are represented by peptides capable of stimulating entry into S phase and, finally, cell division. This is the case with IGFs (Insulin-like Growth Factors) (Pardee 1989, Cross et al. 1991).

IGF-1, in particular, synthesized after stimulation by growth hormone (GH), acts as an endocrine hormone, and may even be considered as the growth hormone (Laron, 2001). Also acting according to a paracrine/autocrine mechanism, this hormone has an important role in children, where it stimulates growth, whereas in adults it increases anabolism.

The specific receptor of this hormone (IGF-1R) is expressed on many different cellular types and therefore several organism's tissues depend on the action of IGF-1: liver, kidneys, lungs, muscles, bone tissue and cartilage, as well as nerve tissue may be mentioned. Moreover, IGF-1 has effects similar to insulin since it can bind—with a low activity—to the insulin receptor, it regulates nerve cells development, and regulates DNA synthesis.

Binding of IGF-1 to the receptor induces an intracellular signal which stimulates cell growth and proliferation (Perona, 2006). This activity makes IGF-1 both a powerful apoptosis inhibitor (programmed cell death) and an activator of protein synthesis (Yanochko et al. 2006, Colòn et al. 2007, Inoue et al. 2005). Finally, in certain conditions, IGF-1 can have the dual role of apoptosis inducer and cell proliferation stimulator (Fu et al. 2007, Rabinovsky 2004 a).

The IGF signalling network has a crucial role in tumour progression, and in metastasis (Hofmann et al. 2005), and many experimental works as well as epidemiological studies establish a significant correlation between a high level of IGF-1 and/or of its receptor and increased risk, or even establishment, of a cancerous proliferation (Vella et al. 2001, Talapatra et al. 2001, Kucab et al. 2003, Kambhampati et al. 2005, Bjorndahl et al. 2005, Gennigens et al. 2006, Velcheti et al. 2006, Yanochko et al. 2006, Sisci et al. 2007, Samani et al. 2007). In general, the role of the GH/IGF-1 axis in oncogenesis and especially in stimulation of tumour progression is therefore well established, as shown in many epidemiological studies and in a very recent study showing that a congenital deficiency of IGF-1 seems to protect against development of cancer (Sheva et al. 2007).

Clinical studies on molecules that inhibit IGF activity show the benefit of their use in various types of cancer, their therapeutic effect acting in synergy with chemotherapy and irradiation (Min et al. 2005, Carmiraud et al. 2005, Chinnavian et al. 2006, Wu et al. 2006, Deutsch et al. 2005, Warshamana-Greene et al. 2005). As IGF-1 is a mediator of the growth hormone, its production can be delayed or inhibited upstream the production of growth hormone (GH), by somatostatin.

Somatostatin (Somatotrope Release Inhibiting Factor, or SRIF), secreted in the hypothalamus, is a natural antagonist of GHRH (neuropeptide stimulating GH synthesis). In particular, by inhibiting GH, SRIF has an inhibitory effect on IGF-1 synthesis. However, SRIF also has a peripheral action, notably by acting as a digestive hormone, inhibiting, for example, the secretion of gastrointestinal and pancreatic hormones.

The SRIF and its synthetic analogues ability to inhibit cell proliferation and to trigger cell death by indirect or direct mechanisms is utilized in several therapeutic protocols of various types of cancers in human medicine. Moreover, SRIF is capable of inhibiting angiogenesis, which is of potential interest in clinical practice for indirect control of tumour growth (Ferjoux et al. 2000). Indeed, tumours obtain nutrients by neovascularization (angiogenesis), and the analogues of SRIF, which inhibit cell proliferation, also have an indirect inhibitory effect on secretion of growth factors such as Vascular Endothelial Growth Factor (VEGF), while reducing monocyte chemotaxis (Dasgupta 2004, Garcia de la Torre et al. 2002).

However, it is only possible to use analogues of SRIF in cancers expressing SRIF receptors. Thus, efficacy of the SRIF analogues used in clinical practice has only been explicitly demonstrated in the treatment of neuroendocrine, gastroenteropancreatic, brain, breast, prostate and lung tumours (Ferjoux et al. 2000). Moreover, one should keep in mind that the level and profile of expression of SRIF receptors vary enormously from one carcinoma to another.

Somatostatin analogues molecules, inhibitors of the "IGF system" (Pawlikowski M. et al., 2004), have already been proposed. These are notably BIM 23A387, Octreotide and Lanreotide (two 8-mer peptides). These molecules modulate receptor or its ligand expression, and are interesting candidates in the treatment of various types of cancer and of acromegaly. Another example, the bispecific synthesis ligand, BIM-23244 (Rani C., 2004, Rani C., 2006, Pandit A., 2008), is capable of inhibiting secretion of growth hormone in somatotrophic adenomas.

SUMMARY OF THE INVENTION

The inventors now propose novel peptides for modulate the effects of IGF-1. These peptides comprise the 20 to 24 amino acids following sequence (I):

$P_a$-$X_1$-Phe-Trp-$X_2$-$X_3$-$P_b$(I)    (SEQ ID NO: 1)

in which:

$P_a$ represents a sequence comprising 10 to 12 amino acids selected from the sequences:

(SEQ ID NO: 3)
Phe-Gly-Ser-Arg-Lys-Phe-Ser-Tyr-Lys-Ala (SEQ ID NO: 4)
Asn-Phe-Gly-Ser-Arg-Lys-Phe-Ser-Tyr-Lys-Ala (SEQ ID NO: 5)
Ser-Asn-Phe-Gly-Ser-Arg-Lys-Phe-Ser-Tyr-Lys-Ala $X_1$ is a lysine, arginine or histidine residue;

$X_2$ is a threonine or lysine residue;

$X_3$ is an aspartate or glutamate residue; and $P_b$ represents a sequence comprising 5 to 7 amino acids selected from the sequences:

```
Val-Thr-Thr-Ser-Glu            (SEQ ID NO: 6)
Val-Thr-Thr-Ser-Glu-Leu        (SEQ ID NO: 7)
Val-Thr-Thr-Ser-Glu-Leu-Gly    (SEQ ID NO: 8)
```

The invention also relates to a peptide resistant to proteolysis derived from sequence (I) by one or more chemical modifications or a substantially homologous peptide derived from sequence (I) by one or more conservative substitution(s).

These peptides are useful for modulate, preferably stimulate, cell proliferation in vitro.

The invention also relates to a pharmaceutical composition comprising at least one such peptide as active ingredient, together with one or more physiologically acceptable excipients.

The present invention also relates to a peptide, as defined here, for use as a medicinal product.

DETAILED DESCRIPTION OF THE INVENTION

Definitions

The term "modulation" refers to an inhibitory and/or activating activity of the peptides of the invention on IGF-1 functions, "Inhibition" means any inhibitory effect on IGF-1 synthesis and/or expression of IGF-1R including an inhibition and/or a down-regulation reducing the activity, activation, functions and/or expression of IGF-1. "Activation" means any effect potentiating, stimulating or activating IGF-1 synthesis and/or the expression of IGF-1R including an activation and/or an up-regulation of the activity, functions and/or expression of IGF-1. An inhibitory and/or activating effect of a peptide is investigated by measuring the expression of IGF-1 and/or of IGF-1R. It is also possible to investigate the inhibition and/or activation induced by a peptide of the invention by means of cell cultures expressing IGF-1 and/or IGF-1R.

The term "patient" refers to any human or non-human animal, preferably a mammal, including male, female, adult and/or child requiring treatment that modulates IGF-1 synthesis and/or the IGF-1 receptor expression.

The term "treatment" or "therapy" comprises both a curative treatment and a prophylactic treatment of a disease. A curative treatment is defined as a treatment resulting in cure or a treatment alleviating, improving and/or eliminating, reducing and/or stabilizing the symptoms of a disease or the suffering that it causes. A prophylactic treatment comprises both a treatment resulting in the prevention of a disease and a treatment reducing and/or delaying the incidence of a disease or the risk of its occurrence.

The expression "conservative substitution" expresses any replacement of an amino acid residue with another, without altering the general conformation or the function of the peptide. Conservative substitution includes, but is not limited to, replacement by an amino acid having similar properties (for example shape, polarity, hydrogen binding potential, acidity, basicity, hydrophobicity etc.). Amino acids having similar properties are well known in the prior art. For example, arginine, histidine and lysine are hydrophilic basic amino acids and can be interchangeable. Similarly, isoleucine, a hydrophobic amino acid, can be replaced with a leucine, a methionine or a valine. The hydrophilic neutral amino acids that can be substituted with one another include asparagine, glutamine, serine and threonine. By "substituted" and "modified" the invention means amino acids that have been altered or modified relative to a natural amino acid. The expression "substantially homologous sequence" comprises any sequence having one or more conservative substitution(s).

Thus, in the context of the present invention, a conservative substitution is known in the prior art as a substitution of one amino acid with another having similar properties. Examples of conservative substitutions are given in Table 1 below:

TABLE 1

Conservative substitutions I

| Side chain characteristic | Amino acid |
| --- | --- |
| Non-polar | G A P I L V |
| Polar-uncharged | C S T M N Q |
| Polar-charged | D E K R |
| Aromatic | H F W Y |
| Other | N Q D E |

As described in Lehninger, 1975, conservative amino acids can also be grouped as shown in Table 2 below:

TABLE 2

Conservative substitutions II

| Characteristics of the side chain | Amino acid |
| --- | --- |
| Non-polar (hydrophobic) | |
| A. Aliphatic: | A L I V P |
| B. Aromatic: | F W |
| C. Sulphur-containing | M |
| D. Other | G |
| Uncharged-polar, | |
| A. Hydroxyl: | S T Y |
| B. Amides: | N Q |
| C. Sulfhydryl: | C |
| D. Other | G |
| Positively charged (basic) | K R H |
| Negatively charged (acid) | D E |

Still another alternative of conservative substitution is presented in Table 3 below:

TABLE 3

Conservative Substitutions III

| Original residue | Example of substitution |
| --- | --- |
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |

TABLE 3-continued

Conservative Substitutions III

| Original residue | Example of substitution |
|---|---|
| Trp (W) | Tyr (Y) |
| Tyr (Y) | Trp (W), Phe (F), Thr (T), Ser (S) |
| Val (V) | Ile (I), Leu (L), Met (M), Phe (F), Ala (A) |

Peptides Preparation:

The peptides according to the invention can be prepared by all standard techniques of peptide synthesis used in the art, namely notably by chemical synthesis or genetic recombination. In a preferred embodiment, the peptides are obtained by chemical synthesis. More preferably, the peptides are obtained either by successive condensation of the amino acid residues in the required order, or by condensation of the residues on a previously formed fragment and already containing several amino acids in appropriate order, or by condensation of several fragments previously prepared, taking care to protect, beforehand, all the reactive functions of the amino acid residues, except the amine and carboxyl functions used in peptide bond during condensation, and notably by the solid-phase synthesis technique of Merrifield.

Properties of the Peptides:

Peptides of the invention can modulate IGF-1 effects. These peptides comprise, or consist of, the 20 to 24 amino acids following sequence (I):

$$P_a\text{-}X_1\text{-}Phe\text{-}Trp\text{-}X_2\text{-}X_3\text{-}P_b(I) \quad \text{(SEQ ID NO: 1)}$$

in which:

$P_a$ represents a sequence comprising 10 to 12 amino acids selected from the sequences:

```
                                    (SEQ ID NO: 3)
Phe-Gly-Ser-Arg-Lys-Phe-Ser-Tyr-Lys-Ala (SEQ ID NO: 4)
Asn-Phe-Gly-Ser-Arg-Lys-Phe-Ser-Tyr-Lys-Ala (SEQ ID NO: 5)
Ser-Asn-Phe-Gly-Ser-Arg-Lys-Phe-Ser-Tyr-Lys-Ala
```

$X_1$ is a lysine, arginine or histidine residue;
$X_2$ is a threonine or lysine residue;
$X_3$ is an aspartate or glutamate residue; and
$P_b$ represents a sequence comprising 5 to 7 amino acids selected from the sequences:

```
    Val-Thr-Thr-Ser-Glu          (SEQ ID NO: 6)

Val-Thr-Thr-Ser-Glu-Leu      (SEQ ID NO: 7)

Val-Thr-Thr-Ser-Glu-Leu-Gly  (SEQ ID NO: 8)
```

The invention also includes a peptide resistant to proteolysis derived from sequence (I) by one or more chemical modifications or a substantially homologous peptide derived from sequence (I) by one or more conservative substitution(s).

Preferably, $X_1$ is a lysine residue, $X_2$ is a threonine residue, and $X_3$ is an aspartate residue.

In a preferred embodiment, the peptide comprises the following amino acid sequence:

```
    SNFGSRKFSYKAKFWTDVTTSELG      (SEQ ID NO: 2)
```

Preferably, the N- and/or C-terminal positions are protected from proteolysis. For example, the N-terminal end can be in the form of an acetyl, and/or the C-terminal end can be in the form of an amide group. Any modification rendering the peptides of the invention resistant is contemplated, for example peptides in which at least one peptide bond is modified and replaced with a ($CH_2NH$) bond, an (NHCO) bond, a ($CH_2$—O) bond, a ($CH_2$—S) bond, a ($CH_2CH_2$) bond, a (CO—$CH_2$) bond, a (CHOH—$CH_2$) bond, an (N—N) bond, an alkene-E bond or a —CH=CH bond.

All peptides chemically modified for resisting to proteolysis are included in the present invention.

For example the above peptide designated P70 can be in the form

```
                                    (SEQ ID NO: 2)
Acetyl-SNFGSRKFSYKAKFWTDVTTSELG-Amide
```

The invention also encompasses substantially homologous peptides derived from sequence (I) by one or more conservative substitution(s). Two amino acid sequences are called "substantially homologous" or "substantially similar" when one or more amino acid residues are substituted with one or more residues that are similar in a biological view, or when more than 80% of the amino acids are identical, or preferably when more than 90% of the residues are identical (functionally identical). The similar or homologous sequences are preferably identified by alignment using, for example, GCG "Pileup" program (Genetics Computer Group, software manual for the GCG Package, Version 7, Madison, Wis.), or any other program known by a person skilled in the art (BLAST, FASTA, etc.).

According to the invention, all amino acid residues of the peptides belong to the L form (levogyral). However, it is also encompassed, whatever the amino acid of sequence (I), to substitute the D form (dextrogyral) for the L form. In particular it is encompassed that some amino acids—those located in positions 11 to 18 in sequence (I) and notably tryptophan in position 15—belong to the D form, for the peptides to be more resistant to peptidases.

Advantageously, peptides are covalently bound to one or more polyethylene glycol (PEG) molecule(s) by their C-terminal terminus or a lysine residue, notably a PEG of 1500 or 4000 MW, for an increase of the half-life in blood plasma and for a decrease in therapeutic doses used. The binding of PEG is as described by Abuchowski et al. (J. Biol. Chenu., 1977, 252: 3582-3586). In a further aspect of the invention, peptides are included in biodegradable polymers or copolymers forming microspheres, for example poly(D,L-lactide-co-glycolide) (PLGA) (as illustrated in US2007/0184015, SoonKap Hahn et al).

Peptides of the invention, different from endogenous (native) somatostatin or from peptides known in the art, exhibit a R-hairpin molecular conformation which is stable in physiological medium as in hydrophobic medium. Advantageously, no condition of the medium can induce a transition of the peptide conformation to α helix.

Moreover, the hairpin conformation enable to expose, in the bend formed by the folding of the peptide sequence, two amino acids (Phe-Trp) out of the four contiguous amino acids (Phe-Trp-Lys-Thr) considered in SRIF as major for binding to receptors. Without being bound by this hypothesis, the inventors believe that in peptide sequences of the invention, an electrostatic attraction between amino acid in position 13 and amino acid in position 17 allowing a conformation "bend"-type, causing the whole peptide to have a conformation of the β type (type VIII β conformation).

Peptides useful herein display bi-phasic effect. Depending on the concentration used peptides are thus able to activate or to inhibit IGF-1 production and expression of its receptor (IGF-1R). In vitro, these effects lead either to stimulation or to inhibition of cell proliferation.

Bi-phasic effect of a biological molecule showing a dose dependent agonist or antagonist effect is well known for other molecules and in various biological systems (enzymes [Gamage et al. 2003, He et al. 2003], ionic channels and co-carriers [Arias et al. 1996, Lombardi et al. 2001, Borst et al. 2002, Incerpi et al. 2003] carriers [Henry et al. 2002], tyrosine kinase receptors [Leiser et al. 1986, Schlessinger 1988], G protein-coupled receptor (GPCRs), neurotransmitters, hormones and chemokines [Winding et al. 1993, Chidiac et al. 1996, Bronnikov et al. 1999, Cuthbert 2003, Hornigold et al. 2003, Griffin et al. 2003, Fuh et al. 1992, Talmadge 1998], in particular concerning GnRH and analogs thereof [Browning J. Y et al. 1983, Ho M. N. et al. 1997, Barbarino A et al. 1982, Imai, A et al. 1993, Kang, Sung K et al. 2000 et 2001, Gründker C et al. 2003, Leung P. C. K et al. 2003, Bhasin S. et al. 2008].

Peptides described herein are useful for stimulating cell proliferation in vitro, for example in keratocytes, chondrocytes or hepatocytes cultures or for the preparation of tissues of medical interest.

With these remarkable properties, peptides described herein are useful in various applications, in vitro and in vivo, notably in human or veterinary medicine.

The peptides of the invention can be used at a suitable dose:
either for stimulating IGF-1 synthesis and/or IGF-1 receptor expression;
or for inhibiting IGF-1 synthesis and/or IGF-1 receptor expression.

Stimulation of IGF-1 synthesis and/or of expression of its receptor is desired in a variety of cases:
when peptides are used as growth hormone substitute. The peptides are particularly useful in all therapeutic indications associated with a complete or partial deficiency, congenital or acquired, of the endogenous growth hormone or of IGF-1, and notably in the treatment of underdevelopment in children or in adults. Other therapeutic applications comprise for example Turner's syndrome, Prader-Willi syndrome, chronic renal insufficiency. The peptides of the invention are particularly useful for disorders where an increase in muscle mass may be required such as cachectic conditions associated with acquired immunodeficiency syndrome (AIDS) or with cancer. Peptides are also useful in the veterinary area, notably in cattle, pigs, sheep, horses etc breeding.

in the therapeutic treatment of metabolic syndrome, such as obesity or type II diabetes (notably by lowering the blood lipid rate and improving glucose metabolism), as well as for stimulating or restoring the immune defences, in particular in elderly or immunodepressed subjects, or for the treatment of autoimmune diseases (such as type I diabetes) and/or neurodegenerative diseases (such as multiple sclerosis).

for stimulating the survival of nerve cells (anti-apoptotic effect), differentiation or neuronal development, regeneration of motor or sensory nerves, synaptogenesis and remyelinization. By stimulating the production of IGF-1, peptides of the invention are therefore used as neurotrophic agents for stimulating neurogenesis and/or as neuroprotective agents (in particular in ischaemic attacks).

Inhibition of IGF-1 synthesis and/or of expression of its receptor is notably desired in the following cases:
when the peptides are used as somatostatin's substitute, like those disorders for which octreotide and lantreotide are indicated. The desired biological effects are for instance inhibition of pituitary GH secretion, inhibition of biliary secretion, inhibition of pancreatic and gastrointestinal exocrine and/or endocrine secretions. For example, peptides are used as somatostatin's substitute for treatment of Alzheimer's disease.

for treatment of acromegaly, particularly in patients who have had an inadequate response to surgery, and/or radiation therapy, and other medical therapies, or for whom these therapies are not appropriate. The goal of treatment is then to normalize serum IGF-1 levels and to improve clinical signs and symptoms.

in treatment of cancer, in particular but not limited to, for the treatment of breast cancer, pancreatic cancer, prostatic cancer, pituitary adenoma or digestive endocrine tumor. Furthermore, peptides may be used for the treatment of metastases (including gastrointestinal metastasis). Also encompassed is the use of peptides of the invention in an inhibitory dose to improve the symptoms associated with digestive endocrine tumor such as diarrhea and flush Pharmaceutical Compositions:

The peptide may be administered by any convenient route including systemic (parenteral, intravenous . . . ), oral, rectal, topical, transdermal, subcutaneous, intrapulmonary (see Agu et al, 2001) and intranasal route. In a preferred embodiment, peptides are administered by intranasal route.

In vitro, an example of suitable dose for stimulating IGF-1 synthesis and/or IGF-1 receptor expression is a dose in a concentration of about $10^{-7}$M, and an example of suitable dose to inhibit IGF-1 synthesis and/or IGF-1 receptor is a dose in a concentration of at least $10^{-6}$M.

Corresponding dosing in vivo is selected by the skilled person with regard to disorders to treat so that desired effect is achieved.

An efficient dose to stimulate IGF-1 synthesis and/or expression of IGF-1 receptor in vivo typically includes a concentration of at least 100 µg daily, preferably from about 10 µg to 100 µg. An efficient dose to inhibit IGF-1 synthesis and/or expression of IGF-1 receptor in vivo typically includes a concentration of at least 300 µg daily, preferably from about 300 µg to 3 mg. Preferably, the efficient daily dosage is from about 1 mg to 3 mg, still more preferably from about 2 mg to 3 mg. For administration via intranasal or intrapulmonary route or if sustained-release formulations are used, stimulating and/or inhibiting doses required can be from 10 to 100 times lower. These administrations can be repeated for long periods, preferably for a period from 3 to 6 months.

Further aspects and advantages of the present invention will be disclosed in the following experimental section, demonstrating the biological activity of a peptide according to the invention The peptide sequence of the invention used in following examples and figures—named P70—contains the following amino acids sequence:

(SEQ ID NO: 2)
Acetyl-SNFGSRKFSYKAKFWTDVTTSELG-amide

These examples should be regarded as illustrative and not limiting the scope of the present application.

LEGENDS OF THE FIGURES

EXAMPLES

Example 1

Effect of a Peptide of the Invention on Cell Proliferation

The biological effects of the peptides of the invention are demonstrated in a chondrocytes primary culture model of neonatal mouse mandibulary.

To assess peptide ability to induce cell proliferation, inventors carried out a test showing [$H^3$] thymidine incorporation during DNA duplication according to Kurz et al., 1997 method. This test was adapted to the model used by the inventors, namely a primary mouse embryonic chondrocytes culture.

Chondrocytes, obtained by dissociation of mouse mandible condyles (MCDC) were incubated in a culture medium permitting chondrogenesis, in particular, $5 \times 10^5$ cells/ml were incubated with 1 µCi [$^3$H]-thymidine/ml of medium (Amersham, code TRA120, stock 1 mCi/ml, specific activity 5 Ci/mmol) for 3 hours at 37° C. in DMEM medium (Dulbecco's modified Eagle's medium) fetal calf serum (FCS) free but supplemented with 100 µg/ml of ascorbic acid, 1 mmol/L of calcium chloride, 10 mmol/L of 3-glycerophosphate, and antibiotics. Same medium, in which 5 µl of [$^3$H]-thymidine are added for 2 minutes, is used as negative control. Supernatant was removed and cells were washed twice with saline solution buffered at pH 7.0 (PBS), the cells are washed twice (for 5 minutes) with methanol. Then the cells are washed three times with a 10% trichloroacetic acid (TCA) cold solution. After washing cells twice with DDW, cells are incorporated in 200 µl of 0.3M NaOH for 15 minutes. The cells are then transferred in 3 ml of a neutralized scintillation fluid with 200 µl of 0.3M HCl. Finally, samples containing the cells were mixed in a vortex, and placed in a beta counter for 1 minute.

Figure 1:
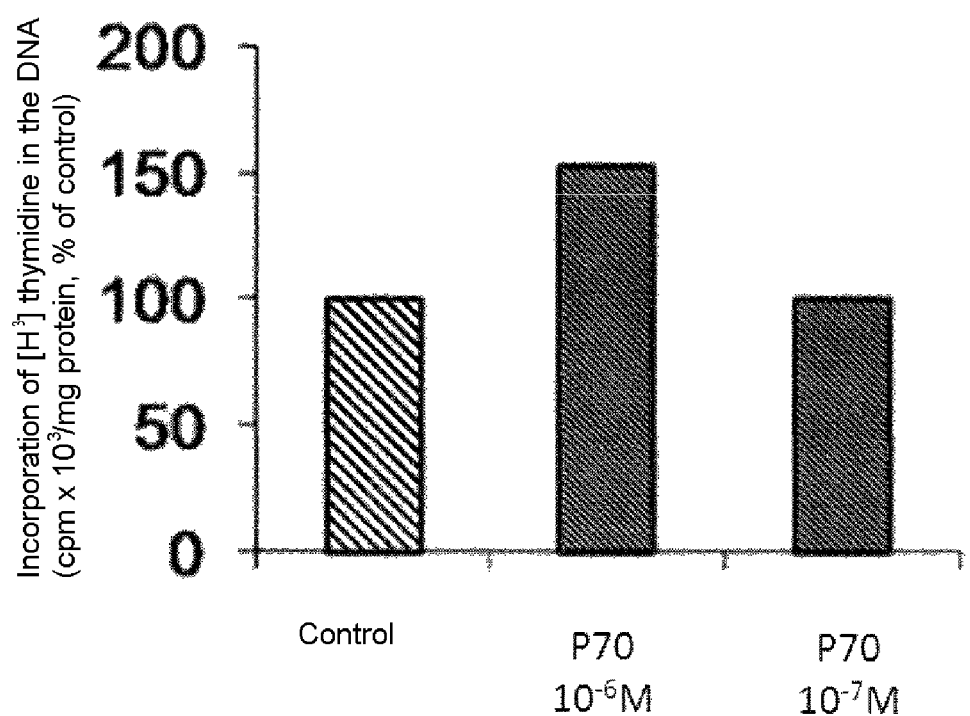
FIG. 1 is a graph that shows P70 effect on incorporation of [$H^3$] thymidine in DNA.

The results obtained show (FIG. 1) that peptide P70 has a stimulatory effect on the proliferation of chondrocytes 53% greater than the untreated control (chondrocytes that have not been incubated with no peptide or other growth factor), at the highest concentration ($10^{-6}$M), whereas this stimulation effect is not observed at a lower concentration ($10^{-7}$M).

Example 2

Figure 2:
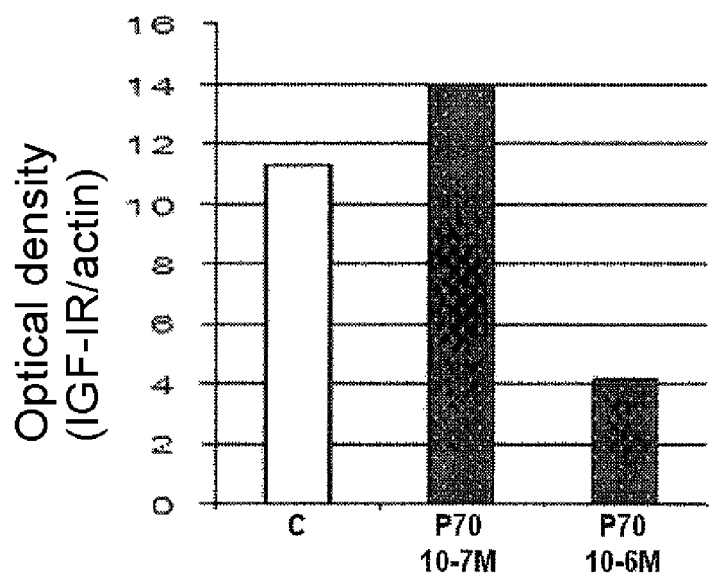
FIG. 2 is a graph that shows P70 effect on expression of IGF-1R assessed by measuring optical density.

Effect of a Peptide of the Invention on IGF1 Synthesis and on IGF1 Receptor Expression Inventors investigated P70 effect on IGF-1 synthesis and on expression of its receptor (IGF-1R) by means of chondrocytes in culture. The inventors show that peptide has an important stimulation effect on IGF-1 production and on expression of its receptor (IGF-1R) when chondrocytes are incubated with a low concentration of peptide ($10^{-7}$ M) (FIG. 2).

Conversely, at a higher concentration ($10^{-6}$M), peptide virtually inhibits the production of IGF-1 and of its receptor.

Using immunohistochemistry (IHC) on a 5-day primary chondrocytes culture (FIG. 3) the inventors also show that peptide P70 inhibits IGF-1 receptor expression at $10^{-6}$ M (36.8% inhibition at a high concentration of peptide) whereas it stimulates expression of same receptor at $10^{-7}$ M (23.8% increase at a low concentration of peptide). Moreover (FIG. 4), P70 inhibits IGF-1 synthesis at $10^{-6}$M (30% inhibition at a high concentration of peptide) and stimulates IGF-1 synthesis at $10^{-7}$M (90% increase at a low concentration of peptide).

Example 3

Effect of a Peptide of the Invention on Cell Differentiation

Figure 5:
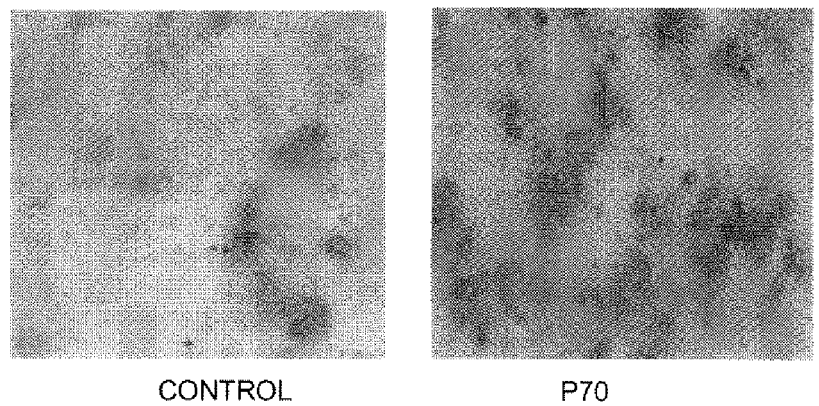
FIG. 5 shows P70 effect on the production of type II collagen in a primary neonatal mouse mandibulary chondrocytes culture, by immunohistochemistry.

The mouse embryos chondrocytes obtained according to same protocol as described above were cultured and incubated at a $10^{-7}$M peptide P70 concentration. At 5th day of culture, the inventors show by immunochemistry (labelling with specific anti-type II collagen antibodies) that the peptide significantly stimulates type II collagen production, a major component of the extracellular matrix useful in the production of articular cartilage (FIG. 5). In fact, an increase of 150% is observed relative to the untreated control.

Figure 6:
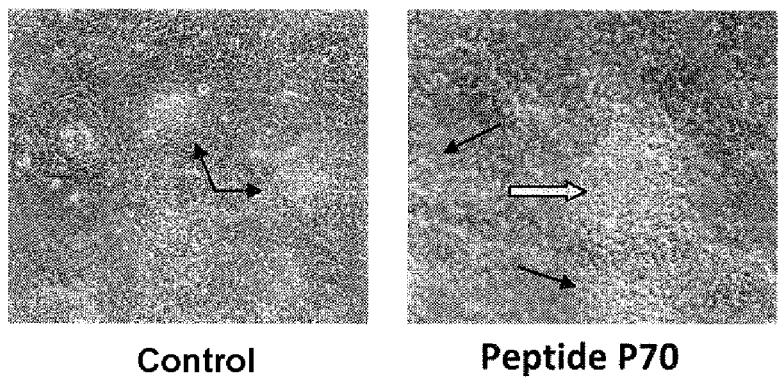
FIG. 6 shows P70 effect on chondrogenesis process in a primary neonatal mouse mandibulary chondrocytes culture. The arrows show the cartilage formation nodules.

In FIG. 6, the peptide P70 effect at a concentration of $10^{-7}$M is compared with untreated chondrocytes (control). At 7th day of incubation, in the presence of the peptide, accelerated formation of nodules of cartilage is clearly observed. The cartilage nodules development (volume/culture) is 85% accelerated.

CONCLUSION

Figure 3:
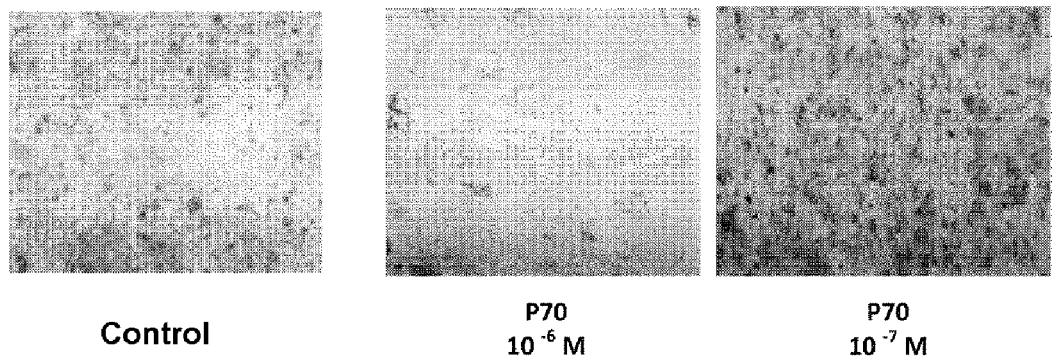
FIG. 3 shows P70 effect on IGF-1R expression in a primary neonatal mouse mandibulary chondrocytes culture, by immunohistochemistry.
Figure 4:
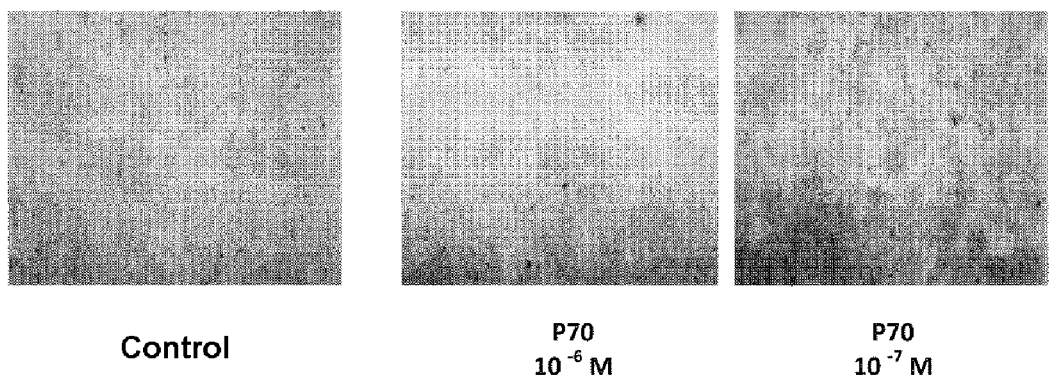
FIG. 4 shows P70 effect on IGF-1 synthesis in a primary neonatal mouse mandibulary chondrocytes culture, by immunohistochemistry.

Peptide P70 displays a bi-phasic profile:
  at low concentration ($10^{-7}$M):
    it stimulates cell differentiation, particularly by accelerating chondrogenesis first phases (see FIG. 5—expression of type II collagen, and FIG. 6—chondrogenesis)
    it stimulates IGF-1 production and IGF-1 receptor expression (see FIG. 2—Optical density, and FIG. 3—immunohistochemistry) and IGF-1 synthesis (see FIG. 4—immunohistochemistry).
  at high concentration ($10^{-6}$M):
    it stimulates cell proliferation (see FIG. 1—incorporation of tritiated thymidine)
    it inhibits IGF-1 production (see FIG. 4—immunohistochemistry) and IGF-1 receptor expression (see FIG. 2—Optical density, and FIG. 3—immunohistochemistry)

REFERENCES

Arias H R: (1996) Agonist self-inhibitory binding site of the nicotinic acetylcholine receptor. J Neurosci Res, 44:97-105.

Agu R U, Ugwoke M I, Armand M, Kinget R, Verbeke N. The lung as a route for systemic delivery of therapeutic proteins and peptides. *Respir Res.* 2001; 2(4):198-209. Epub 2001 Apr. 12

Barbarino A, De Marinis L., Mancini A., Giustacchini M., Alcini A. E. (1982) Biphasic effect of estradiol on luteinizing hormone response to gonadotropin-releasing hormone in castrated men, Metabolism 31(8):755-8

Bhasin S, Heber D, Steiner B, Peterson M, Blaisch B, Campfield L A, Swerdloff R. S. (2008) Hormonal effects of GnRH agonist in the human male: II. Testosterone enhances gonadotrophin suppression induced by GnRH agonist. Clinical Endocrinology 20: 119-128

Bjorndahl M. et al. (2005). "Insulin-like growth factor 1 and 2 induce lymphangiogenesis in vivo. PNAS USA 102, 15593-15598.

Borst P, Elferink R O: Mammalian ABC transporters in health and disease. Annu Rev Biochem 2002, 71:537-592.

Bronnikov G E, Zhang S J, Cannon B, Nedergaard J (1999) A dual component analysis explains the distinctive kinetics of cAMP accumulation in brown adipocytes. J Biol Chem, 274:37770-37780.

Browning J. Y., R. D'Agata, A. Steinberger, H. E. Grotjan Jr and E. Steinberger (1983) Biphasic effect of gonadotropin-releasing hormone and its agonist analog (HOE766) on in vitro testosterone production by purified rat Leydig cells, Endocrinology, Vol 113, 985-991

Camiraud A. et al. (2005). "Inhibition of insulin-like growth factor-1 receptor signalling enhances growth-inhibitory and proapoptotic effects of gefitinib (Iressa) in human breast cancer cells". Breast Cancer Res. 7, R570-579.

Cassoni P. et al. (2006). "Grelin and cortistatin in lung cancer: expression of peptides and related eceptors in human primary tymors in vitro effect on the H345 small cell carcinoma cell line". J. Endocrinol. Invest. 29, 781-790.

Chidiac P, Nouet S, Bouvier M (1996) Agonist-induced modulation of inverse agonist efficacy at the beta 2-adrenergic receptor. Mol Pharmacol, 50:662-669.

Chinnavian P. et al. (2006). "Radiation and new molecular agents, pert II: targeting HDAC, HSPçà, IGF-1R, PI3K, and Ras". Semin. Radiat. Oncol. 16, 59-64.

Colòn E. et al. (2007) Insulin-like growth factor-I is an important antiapoptotic factor for rat leydig cells during postnatal development. Endocrinology 148, 128-139.

Cross M., T. M. Dexter (1991). "Growth factors in development, transformation, and tumorigenesis". Cell 64, 271-280

Cuthbert A W: (2003) Benzoquinolines and chloride secretion in murine colonic epithelium. Br J Pharmacol, 138: 1528-1534.

Dasgupta 2004, (2004) <<Somatostatin analogues: multiple roles in cellular proliferation, neoplasia, and angiogenesis>> Pharmacol Ther 102 (1): 61-85

Deutsch E. et al. (2005). "New strategies to interfere with radiation response: "biomodulation" of radiation therapy". Cancer Radiother. 9, 69-76.

Ferjoux G., C. Bousquet, P. Cordelier et al. (2000). "Signal transduction of somatostatin receptors negatively controlling cell proliferation". J. Physiol. (Paris) 94, 205-210.

Fu P. et al. (2007). "Insulin-like growth factor induces apoptosis as well as proliferation in LIM1215 colon cancer cells". J. Cell. Biochem. 100, 56-68.

Fuh G, Cunningham B C, Fukunaga R, Nagata S, Goeddel D V, Wells J A (1992) Rational design of potent antagonists to the human growth hormone receptor. Science, 256:1677-80.

Gamage N U, Duggleby R G, Barnett A C, Tresillian M, Latham C F, Liyou N E, McManus M E, Martin J L (2003) Structure of a human carcinogen-converting enzyme, SULT1A1. Structural and kinetic implications of substrate inhibition. J Biol Chem, 278:7655-7662

Garcia de la Torre N, Wass J A, Turner H E, (2002) <<Antiangiogenic effects of somatostatin analogues" Clin Endocrinol 2002 57(4): 425-441 Review Gennigens C., C. Menetrier-Caux, J. P. Droz (2006). "Insulin-like growth factor (IGF) family and prostate cancer". Crit. Rev. Oncol. Hematol. 58, 124-145

Griffin M T, Hsu J C, Shehnaz D, Ehlert F J: Comparison of the pharmacological antagonism of M2 and M3 muscarinic receptors expressed in isolation and in combination. Biochem Pharmacol 2003, 65:1227-1241.

Gründker C. and G. Emons (2003) Role of gonadotropin-releasing hormone (GnRH) in ovarian cancer. Reproductive Biology and Endocrinology 1:65

Hanahan D., R. A. Weinberg (2000). "The hallmarks of cancer". Cell 100, 57-70.

He Y A, Roussel F, Halpert J R (2003) Analysis of homotropic and heterotropic cooperativity of diazepam oxidation by CYP3A4 using site-directed mutagenesis and kinetic modeling. Arch Biochem Biophys, 409:92-101.

Henry E R, Bettati S, Hofrichter J, Eaton W A (2002) A tertiary two-state allosteric model for hemoglobin. Biophys Chem, 98:149-164.

Ho M. N., Delgado C. H., Owens G. A., Steller M. A. (1997) Insulin-like growth factor-II participates in the biphasic effect of a gonadotropin-releasing hormone agonist on ovarian cancer cell growth, Fertility and Sterility Volume 67, Number 5, May 1997, pp. 870-876(7)

Hofmann F., C. Garcia-Echeverria (2005). "Blocking insulin-like growth factor-I receptor as a strategy for targeting cancer". DDT 10, 1041-1047.

Hornigold D C, Mistry R, Raymond P D, Blank J L, Challiss R A (2003) Evidence for cross-talk between M2 and M3 muscarinic acetylcholine receptors in the regulation of second messenger and extracellular signal-regulated kinase signalling pathways in Chinese hamster ovary cells. Br J Pharmacol, 138:1340-1350.

Imai, A, Iida, K, Tamaya, T (1993) Gonadotropin-releasing hormone has a biphasic action on aromatase activity through protein kinase C in granulosa cells. Int-J-Fertil-Menopausal-Stud. 38(1): 50-56

Incerpi S, D'Arezzo S, Marino M, Musanti R, Pallottini V, Pascolini A, Trentalance A (2003) Short-term activation by low 17beta-estradiol concentrations of the Na+/H+ exchanger in rat aortic smooth muscle cells: physiopathological implications. Endocrinology, 144:4315-4324.

Inoue A. et al. (2005). "Insulin-growth factor-I stimulated DNA replication in mouse endometrial stromal cells". J. Reprod. Dev. 51, 305-313.

Kambhampati S. et al. (2005). "Growth factors involved in prostate carcinogenesis". Front. Biosci. 10, 1355-1367.

Kang, Sung K.; Cheng, Kwai W.; Nathwani, Parimal S.; Choi, Kyung-Chul; Leung, Peter C. K. (2000) Autocrine Role of Gonadotropin-Releasing Hormone and Its Receptor in Ovarian Cancer Cell Growth. Endocrine. 13(3):297-304

Kang S. K., C-J Tai, P S, Nathwani and P. C. K. Leung (2001) Differential regulation of two forms of Gonadotrophin-related hormone messenger ribonucleic acid in human granulosa-luteal cells. Endocrinology 142: 1182-1192

Kucab J. E., S. E. Dunn (2003). "Role of IGF-1R in mediating breast cancer invasion and metastasis". Breast Dis. 17, 41-47

Kurz B, Schünke M, (1997) <<Articular chondrocytes and synoviocytes in culture: influence of antioxidants on lipid peroxidation and proliferation." Ann. Anat. 1997, 179: 439-446

Laron Z. (2001). "Insulin-like growth factor 1 (IGF-1): a growth hormone". J. Clin. Pathol. Mol. Pathol. 54, 311-316.

Lehninger, (1975) Biochemistry, Second Edition, Worth Publishers, Inc. New-York: NY., pp. 71-77.

Leiser J, Conn P M, Blum J J: (1986) Interpretation of dose-response curves for luteinizing hormone release by gonadotropinreleasing hormone, related peptides, and leukotriene C4 according to a hormone/receptor/effector model. Proc Natl Acad Sci U S A, 83:5963-7.

Leung P. C. K., C. K. Cheng and Z. Xiao-Ming (2003) Multifactorial role of GnRH-I and GnRH-II in the human ovary. Molecular and Cellular Endocrinology 202: 145-153

Lombardi G, Dianzani C, Miglio G, Canonico P L, Fantozzi R: Characterization of ionotropic glutamate receptors in human lymphocytes. Br J Pharmacol 2001, 133:936-944.

Min Y. et al. (2005). "Insulin_like growth factor I receptor blockade enhances chemotherapy and radiation responses and inhibits tumor growth in human gastric cancer xenografts". Gut 54, 591-60.

Moyse E. et al. (1985). "Somatostatin receptors in human growth hormone and prolactin-secreting pituitary adenomas". J. Clin. Endocrinol. Metab. 61, 98-103.

Pandit A., fay N., Border L., Valéry C., Cherif-Cheikh R., Robert B., Artzner F., Paternoster M. J. (2008) Pept. Sci., 14, 66-75.

Pardee A. B. (1989). "G1 events and regulation of cell proliferation". Science 246, 603-608

Pawlikowski M. et Malen-Mucha G. Current Opinion in Pharmacology (2004), 4, 608-613.

Perona R. (2006). "Cell signaling: growth factors and tyrosine kinase receptors". Clin. Transl. Oncol. 8, 77-821.

Rabinovsky E. D. (2004). "The multifunctional role of IGF-1 in peripheral nerve regeneration". Neurol. Res. 26, 204-210.

Rani C., Durrer L., Koerber S. C., Erchegyi J., Reubi J. C., Rivier J., Riek R. J. Med. Chem. (2004), 48, 523-533

Rani C., Durrer L., Koerber S. C., Erchegyi J., Reubi J. C., Rivier J., Riek R. J. Med. Chem. (2006), 49, 4487-4496

Samani A. A. et al. (2007). "The Role of the IGF System in Cancer Growth and Metastasis: Overview and Recent Insights". Endocrine Reviews 28, 20-47.

Schlessinger J (1998) Signal transduction by allosteric receptor oligomerization. Trends Biochem Sci, 13:443-447.

Shevah O., Z. Laron (2007). "Patients with congenital deficiency of IGF-I seem protected from the development of malignancies: A preliminary report". Growth Horm IGF Res. 17, 54-57.

Sisci D., E. Surmacz (2007). "Crosstalk between IGF Signaling and Steroid Hormone Receptors in Breast". Cancer Curr. Pharm. Des. 13, 705-717.

Talapatra S., C. B. Thmpson (2001). "Growth factor Signaling in Cell Survival: Implications for Cancer". Treatment JPET, 298, 873-878.

Talmadge J E (1998) Pharmacodynamic aspects of peptide administration biological response modifiers. Adv Drug Deliv Rev, 241-252

Velcheti V, Govindan R (2006). "Insulin-like growth factor and lung cancer". Journal of thoracic oncology: official publication of the International Association for the Study of Lung Cancer 1 (7): 607-10.

Vella V. et al. (2001). "The IGF system in thyroid cancer: new concepts". J. Clin. Pathol.: Mol. Pathol. 54, 121-125

Warshamana-Greene G. S. et al. (2005). "The insulin-like growth factor-I receptor kinase inhibitor, NVP-ADW742, sensitized small cell lung cancer cell lines to the effects of chemotherapy". Clin. Cancer. Res. 11, 1563-1571.

Winding B, Bindslev N (1993) Desensitization and reactivation of ACh-regulated exocrine secretion in hen tracheal epithelium. Am J Physiol, 264:C342-C351.

Wu X. Z., D. Chen, G. R. Xie (2007). "Bone marrow-derived cells: roles in solid tumor". Neoplasma 54, 1-6.

Yanochko G. M., W. Eckhart (2006). "Type I insulin-like growth factor receptor overexpression induces proliferation and anti-apoptotic signaling in a three-dimensional culture model of breast epithelial cells". Breast Cancer Res. 8, R18.

The invention claimed is:

1. An isolated peptide comprising the 20 to 24 amino acids following sequence (I):

$P_a$-$X_1$-Phe-Trp-$X_2$-$X_3$-$P_b$(I)    (SEQ ID NO: 1)

in which:

$P_a$ represents a sequence comprising 10 to 12 amino acids selected from the sequences:

```
                                     (SEQ ID NO: 3)
Phe-Gly-Ser-Arg-Lys-Phe-Ser-Tyr-Lys-Ala (SEQ ID NO: 4)
Asn-Phe-Gly-Ser-Arg-Lys-Phe-Ser-Tyr-Lys-Ala (SEQ ID NO: 5)
Ser-Asn-Phe-Gly-Ser-Arg-Lys-Phe-Ser-Tyr-Lys-Ala
```

$X_1$ is a lysine, arginine or histidine residue;

$X_2$ is a threonine or lysine residue;

$X_3$ is an aspartate or glutamate residue; and $P_b$ represents a sequence comprising 5 to 7 amino acids selected from the sequences:

```
Val-Thr-Thr-Ser-Glu         (SEQ ID NO: 6)

Val-Thr-Thr-Ser-Glu-Leu     (SEQ ID NO: 7)

Val-Thr-Thr-Ser-Glu-Leu-Gly;   (SEQ ID NO: 8)
or
``` a peptide resistant to proteolysis derived from sequence (I) by one or more chemical modification(s).

2. The isolated peptide according to claim 1, in which $X_1$ is a lysine residue, $X_2$ is a threonine residue and $X_3$ is an aspartate residue.

3. The isolated peptide according to claim 1, comprising sequence SNFGSRKFSYKAKFWTDVTTSELG SEQ ID NO: 2.

4. A pharmaceutical composition comprising the isolated peptide according to claim 1 as active ingredient, together with one or more pharmaceutically acceptable excipients.

5. The isolated peptide of claim 1, wherein the N-terminal end includes an acetyl group, the C-terminal end includes an amide group, or at least one peptide bond is replaced with a ($CH_2NH$) bond, an (NHCO) bond, a ($CH_2$—O) bond, a ($CH_2$—S) bond, a ($CH_2CH_2$) bond, a (CO—$CH_2$) bond, a (CHOH—$CH_2$) bond, an (N—N) bond, an alkene-E bond, or a —CH=CH bond.

6. An isolated peptide consisting of the amino acid sequence of SEQ ID NO: 2.

7. A method for stimulating IGF-1 synthesis and/or IGF-1 receptor expression, which method comprises administering an effective amount of the isolated peptide of claim 1 in a patient at a dose suitable for stimulating IGF-1 synthesis and/or IGF-1 receptor expression.

8. The method of claim 7, wherein the isolated peptide is administered in vivo in an efficient daily dose of less than 100 µg.

9. A method for inhibiting IGF-1 synthesis or IGF-1 receptor expression, which method comprises administering an effective amount of the isolated peptide of claim 1 in a patient at a dose suitable to inhibit IGF-1 synthesis and/or IGF-1 receptor expression.

10. The method of claim 9, wherein the isolated peptide is administered in vivo in an effective daily dose of at least 300 µg per day.

* * * * *

SEQUENCE LISTING

```
<160> NUMBER OF SEQ ID NOS: 8

<210> SEQ ID NO 1
<211> LENGTH: 7
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is a sequence comprising 10 to 12 amino
      acids selected from: Phe-Gly-Ser-Arg-Lys-Phe-Ser-Tyr-Lys-Ala (a),
      Asn+(a), Ser-Asn+(a), or a substantially homologous sequence
<220> FEATURE:
<221> NAME/KEY: MISC_FEATURE
<222> LOCATION: (2)..(2)
<223> OTHER INFORMATION: Xaa is a lysine, arginine or histidine residue
<220> FEATURE:
<221> NAME/KEY: MISC_FEATURE
<222> LOCATION: (5)..(5)
<223> OTHER INFORMATION: Xaa is a threonine or lysine residue
<220> FEATURE:
<221> NAME/KEY: MISC_FEATURE
<222> LOCATION: (6)..(6)
<223> OTHER INFORMATION: Xaa is a aspartate or glutamate residue
<220> FEATURE:
<221> NAME/KEY: MISC_FEATURE
```

```
<222> LOCATION: (7)..(7)
<223> OTHER INFORMATION: Xaa is a sequence comprising 5 to 7 amino acids
      selected from: Val-Thr-Thr-Ser-Glu, Val-Thr-Thr-Ser-Glu-Leu,
      Val-Thr-Thr-Ser-Glu-Leu-Gly, or a substantially homologous
      sequence

<400> SEQUENCE: 1

Xaa Xaa Phe Trp Xaa Xaa Xaa
1               5

<210> SEQ ID NO 2
<211> LENGTH: 24
<212> TYPE: PRT
<213> ORGANISM: artificial sequence
<220> FEATURE:
<223> OTHER INFORMATION: Synthetic polypeptide

<400> SEQUENCE: 2

Ser Asn Phe Gly Ser Arg Lys Phe Ser Tyr Lys Ala Lys Phe Trp Thr
1               5                   10                  15

Asp Val Thr Thr Ser Glu Leu Gly
            20

<210> SEQ ID NO 3
<211> LENGTH: 10
<212> TYPE: PRT
<213> ORGANISM: artificial sequence
<220> FEATURE:
<223> OTHER INFORMATION: Synthetic polypeptide

<400> SEQUENCE: 3

Phe Gly Ser Arg Lys Phe Ser Tyr Lys Ala
1               5                   10

<210> SEQ ID NO 4
<211> LENGTH: 11
<212> TYPE: PRT
<213> ORGANISM: artificial sequence
<220> FEATURE:
<223> OTHER INFORMATION: Synthetic polypeptide

<400> SEQUENCE: 4

Asn Phe Gly Ser Arg Lys Phe Ser Tyr Lys Ala
1               5                   10

<210> SEQ ID NO 5
<211> LENGTH: 12
<212> TYPE: PRT
<213> ORGANISM: artificial sequence
<220> FEATURE:
<223> OTHER INFORMATION: Synthetic polypeptide

<400> SEQUENCE: 5

Ser Asn Phe Gly Ser Arg Lys Phe Ser Tyr Lys Ala
1               5                   10

<210> SEQ ID NO 6
<211> LENGTH: 5
<212> TYPE: PRT
<213> ORGANISM: artificial sequence
<220> FEATURE:
<223> OTHER INFORMATION: Synthetic polypeptide

<400> SEQUENCE: 6

Val Thr Thr Ser Glu
1               5
```

```
<210> SEQ ID NO 7
<211> LENGTH: 6
<212> TYPE: PRT
<213> ORGANISM: artificial sequence
<220> FEATURE:
<223> OTHER INFORMATION: Synthetic polypeptide

<400> SEQUENCE: 7

Val Thr Thr Ser Glu Leu
1               5

<210> SEQ ID NO 8
<211> LENGTH: 7
<212> TYPE: PRT
<213> ORGANISM: artificial sequence
<220> FEATURE:
<223> OTHER INFORMATION: Synthetic polypeptide

<400> SEQUENCE: 8

Val Thr Thr Ser Glu Leu Gly
1               5
```